United States Patent [19]

Arfman et al.

[11] Patent Number: 4,869,876
[45] Date of Patent: Sep. 26, 1989

[54] MULTI-PURPOSE PLURAL-OVEN GAS CHROMATOGRAPHY SYSTEM WITH SHARED CONTROLS

[75] Inventors: Kenneth D. Arfman, Pound Ridge, N.Y.; Theodore J. Pillera, II, Rochester, Minn.; Raymond R. Ruckel, Garrison; Allan C. Turits, Poughkeepsie, both of N.Y.; John Q. Walker, Brookfield Center, Conn.

[73] Assignee: International Business Machines Corp., Armonk, N.Y.

[21] Appl. No.: 605,433

[22] Filed: Apr. 30, 1984

[51] Int. Cl.$^4$ ............................................. G01N 30/02
[52] U.S. Cl. ................................. 422/89; 55/197; 55/386; 73/23.1; 364/497; 436/161
[58] Field of Search .............. 422/89; 55/386, 197; 73/23.1; 436/161; 364/497

[56] References Cited

U.S. PATENT DOCUMENTS

| | | | |
|---|---|---|---|
| 3,550,429 | 12/1970 | MacMurtrie et al. | 55/197 |
| 3,753,653 | 8/1973 | Brieva et al. | 422/89 |
| 3,841,059 | 10/1974 | McCabe | 55/386 |
| 4,057,998 | 11/1977 | Moreaux | 73/23.1 |
| 4,088,986 | 5/1978 | Boucher | 340/237 S |
| 4,344,917 | 8/1982 | Schorno | 422/78 |
| 4,391,778 | 7/1983 | Andersen et al. | 422/89 |
| 4,470,832 | 9/1984 | Sugawara et al. | 55/197 |

FOREIGN PATENT DOCUMENTS

| | | | |
|---|---|---|---|
| 2629048 | 1/1977 | Fed. Rep. of Germany | 55/197 |
| 2923445 | 12/1979 | Fed. Rep. of Germany | 55/197 |
| 42-13997 | 8/1967 | Japan | 436/161 |

OTHER PUBLICATIONS

Siemens; Sichromat: The Gas Chromatograph with the Convincing Technology (products publication) (undated).
Siemens; Sichromat 2 The GC with Two Ovens (products publication) (undated).
Karasek; Combined Concepts Lead to Automated GC System; Industrial Research & Development, Mar. 1981, pp. 130–134.

*Primary Examiner*—Robert J. Hill, Jr.
*Attorney, Agent, or Firm*—D. R. McKechnie

[57] ABSTRACT

A gas chromatography (GC) system includes a primary complete, independently-operable, self-contained GC system and a secondary, dependently-operable GC system. The primary and secondary systems have two independently controlled GC ovens. Injectors and detectors are supported by heater blocks or ovens mounted on the respective GC ovens and are connected to the electrical and pneumatic controls of the primary GC system. The injectors and detectors of the secondary GC system share operation of the primary GC system. GC columns can be mounted in each oven and operated completely independently or dependently in different ways. A separate power supply for the secondary oven is connectable to a separate circuit or power line in the user environment.

8 Claims, 5 Drawing Sheets

MULTI-PURPOSE PLURAL-OVEN GAS CHROMATOGRAPHY SYSTEM WITH SHARED CONTROLS

This invention relates to gas chromatography and, more particularly, to a gas chromatography (GC) system having two independently accessible GC ovens and different detector-injector-column configurations providing multiple modes or ways to separate and analyze samples.

BACKGROUND OF THE INVENTION

There are a number of commercially available gas chromatography systems each of which has a single electrically heated GC oven enclosing a separating column. The column is connected at one end to a sample injector mounted on the oven in a heated injector block which forms an injector oven. The other end of a column is connected to a detector which also is mounted on the oven in a heated block or oven. An electrical system controls heating of the oven, the detector and the injector and also processes the signal from the detector. The electrical system further includes a data system which controls operation of the GC system, analyzes the signal and outputs data from the system.

Systems of the above type are normally operated at either a constant temperature or at predetermined or programmed temperatures in order to separate a sample as desired. An additional column and other detectors and injectors may also be used to provide such a system with a wide variety of different configurations and ways to analyze a sample.

Also known in the prior art is a GC system having a dual oven formed by an enclosure having a bottom wall, a top wall and a four-sided vertically movable side wall or mantle movable between an open and close position. When the mantle is closed, a partition divides the thus formed chamber into two ovens which are independently controlled as to temperature to provide different ways, in conjunction with different column, detector and injector configurations, in much the same manner as the present invention provides. The ovens are not independently accessible but are both either open or closed at the same time. Further, when cooling is used, both ovens are cooled simultaneously as opposed to separately. The system includes the gas control system and an electrical system including a data system. The partition is removable so that a single oven can be formed to accommodate longer columns.

SUMMARY OF THE INVENTION

One of the objects of the invention is to provide a GC system having two GC ovens which can be operated in a completely independent fashion or in a dependent fashion, in conjunction with different configurations of injectors, columns, and detectors, to provide a highly versatile system operable in many different ways to analyze various samples.

Another object of the invention is to provide a GC system having two sub-systems or systems, one of which is a completely self-contained stand-alone GC system and the other of which is an add-on dependent system that is connected to the first system and shares some of the controls both electrically and pneumatically, to reduce the overall cost of the complete system.

Briefly, the manner in which the above and other objects and advantages of the invention are attained, is to provide a GC system formed from a primary complete, independently-operable, self-contained GC system and a secondary, dependently-operable GC system. The primary and secondary systems have two independently controlled GC ovens. Injectors and detectors are supported by heater blocks or ovens mounted on the respective GC ovens and are connected to the electrical and pneumatic controls of the primary GC system. The injectors and detectors of the secondary GC system share operation of the primary GC system. GC columns can be mounted in each oven and operated completely independently or dependently in different ways. A separate power supply for the secondary oven is connected to a separate circuit or power line in the user environment so as to not require a higher capacity power line, for operation.

BRIEF DESCRIPTION OF THE DRAWINGS

Other objects and advantages of the invention will be apparent from the following description of a preferred embodiment of the invention, taken in connection with accompanying drawings wherein.

DETAILED DESCRIPTION OF THE DRAWINGS

Figure 1:
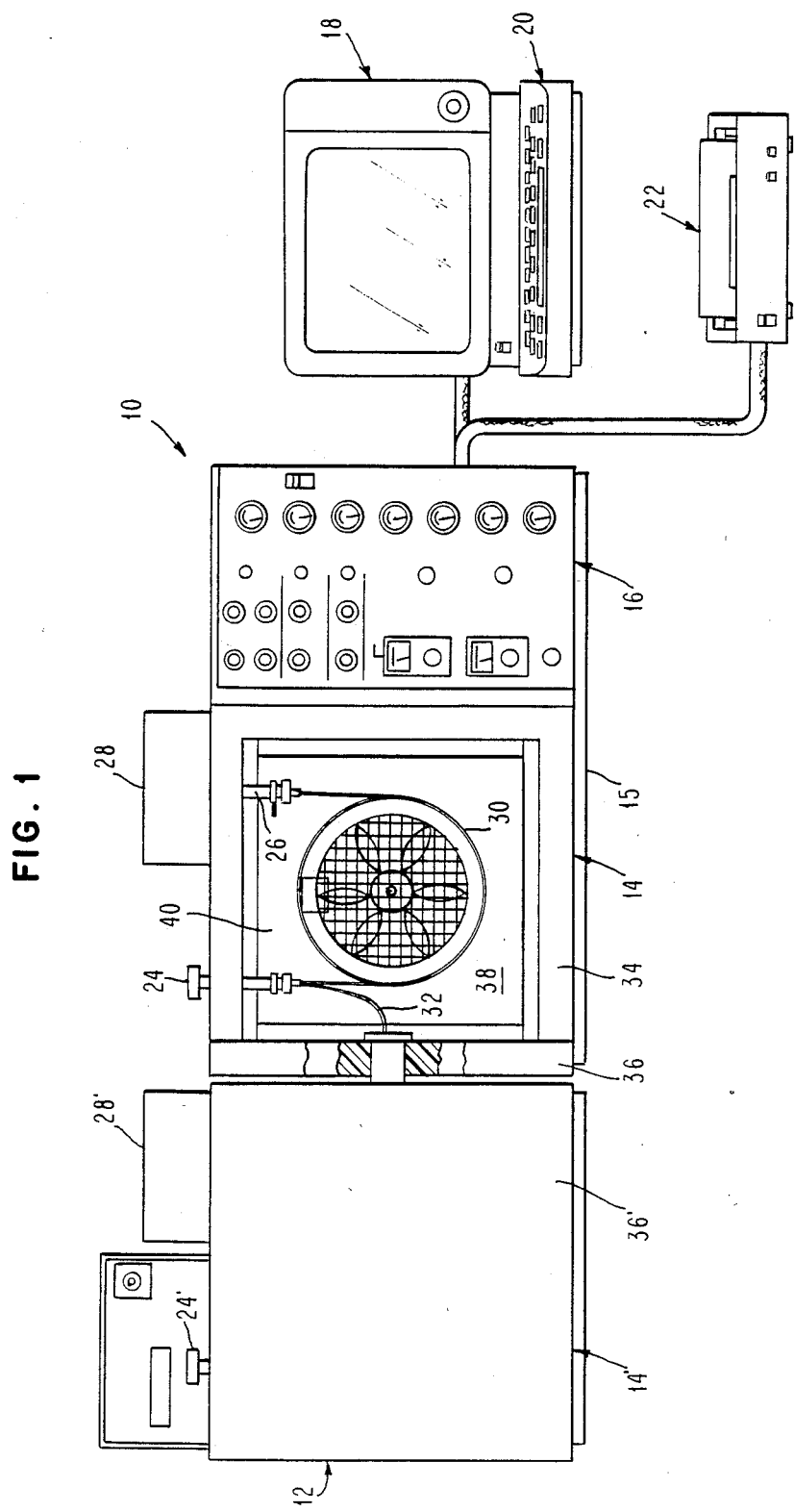
FIG. 1 is a front elevational view, partly schematic, and partly in section with portions removed, of a GC system embodying the invention.

Referring now to the drawings, and first to FIG. 1, the plural or multiple oven GC system of the invention comprises a primary GC system 10 connected to a secondary GC system 12. System 10 is a completely self-contained system capable of independently performing a wide variety of chromatography analyses in the same manner as many commercially available single oven GC systems. System 10 (referred to hereinafter as GC 10) comprises a GC oven 14 and a electrical/pneumatic section 16 mounted on a common base 15, a display 18, a keyboard 20, and an integrator/plotter 22. System 12 (hereinafter referred to as GC 12) comprises a GC oven 14' substantially identical to oven 14.

GC 10 also includes an injector 24 mounted on the top wall of oven 14 in a heater block or oven similar to oven 27 described below. Injector 24 may be one of several different types: a universal packed column injector suitable for on-column and flash vaporization injection, a universal capillary injector suitable for split, splitless and solid effect injection, and an on-column injector for direct injection into a capillary column, etc.

Figure 2:
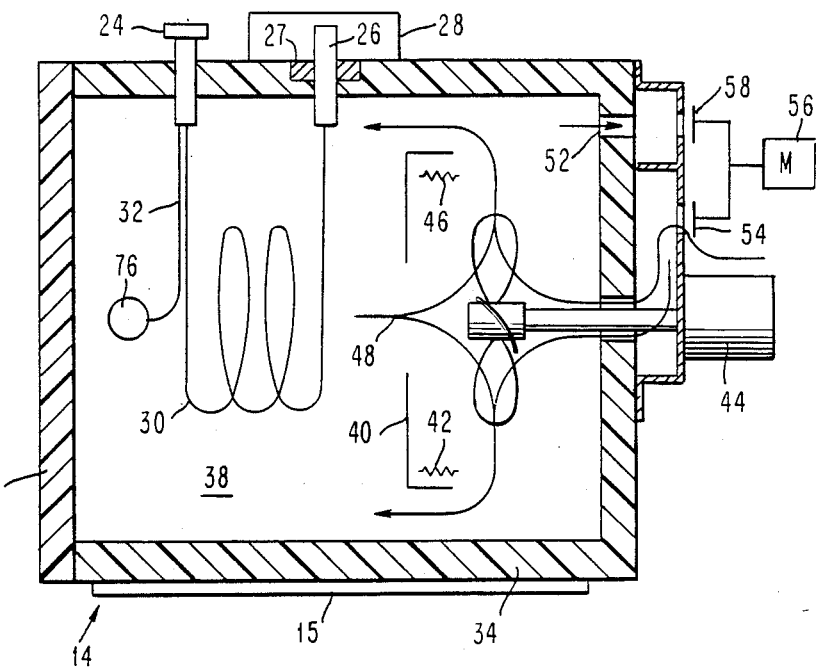
FIG. 2 is a schematic sectional view, illustrating further aspects of the interior of one of the ovens in the GC system of FIG. 1.

GC 10 also includes a detector 26 mounted on the top wall of oven 14 by a heater block or oven 27 (FIG. 2). Detector 26 extends through block 27. The block contains an electric heater 96 (FIG. 9) and forms a detector oven, the temperature of which is controlled, in a manner described hereinafter, to maintain the detector at a desired temperature. The upper end of the detector is covered by a cover 28 protecting the detector, during operation, from the effects of any eddy currents or turbulence in the ambient atmosphere. Detector 26 may be any well known type such as a flame ionization detector (FID), an electron capture detector (ECD), a thermal conductivity detector (TCD), a nitrogen/phosphorous specific detector (NPD), a flame photometric detector (FPD), etc. GC 10 may also use different GC columns such as a packed column or a high resolution capillary column. FIG. 1 illustrates the use of a coiled capillary column 30 connected at one end to injector 24 and at its other end to detector 26. As is well known in the art, the selection of which types of detector, injector and column to use is dependent upon the nature of the sample being analyzed and its expected constituents. At any given time, up to four injectors 24 can be mounted on oven 14 and up to three detectors 26 along with three columns, may be used in GC 10. By use of a universal injector 24, a second capillary column 32 can be connected at one end to injector 24 so that the flow of the injected sample and carrier gas splits to flow through both columns 30 and 32.

Ovens 14 and 14' are substantially identical in structure and will be explained with reference to the construction of oven 14 as best seen in FIGS. 1 and 2. Corresponding parts of oven 14' are indicated with primed reference numerals. Oven 14 has a cubical shape formed by an insulated enclosure 34 having five walls (top and bottom walls, a rear wall, and left and right side walls as viewed from the front). An insulated door 36 is mounted on enclosure 34 and is movable between an open position (shown in FIG. 1) which provides access to the oven chamber 38, and a closed position (FIG. 2) which completely closes off and contains oven chamber 38.

Mounted in oven chamber 38 behind the space containing column 30 is a transverse baffle 40 of sheet metal having a central opening covered by a protective grid. Baffle 40 is square shaped and is connected at its four corners by rods to the interior side walls of enclosure 34. The dimensions of baffle 40 are less than that of the corresponding dimensions of chamber 38 to provide a peripheral space permitting air to flow from the rear of the oven compartment towards the front as shown by arrow 48 in FIG. 2. A fan 42 is mounted behind baffle 40 and is surrounded by an oven heater 46. Fan 42 is driven by a motor 44. Air is normally sucked in from the front of the baffle through the central opening in baffle 40 and is thrown outwardly by fan 42, across heaters 46 and thence forwardly into the front portion of chamber 38. The baffle creates turbulence and provides thorough mixing to insure a uniform temperature within chamber 38.

An air intake port 50 extends through the center of the rear wall of enclosure 32 to admit cool ambient air into the center part of the oven chamber when a flap 54, controlled by motor 56 is actuated. An exhaust port 52 allows heated air from the enclosure to be dumped into the ambient atmosphere when a flap 58, also controlled by motor 56, is open. The simultaneous opening and closing of flaps 54 and 58 along with regulation of heater 46 are used to regulate the desired temperature within the oven.

Figures 3, 4:
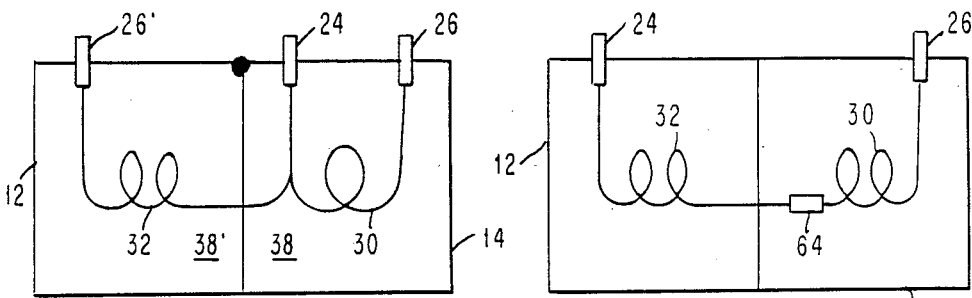
FIGS. 3-5 are schematic views illustrating different injector, column, detector configurations, for understanding how the invention might be used.
Figure 5:
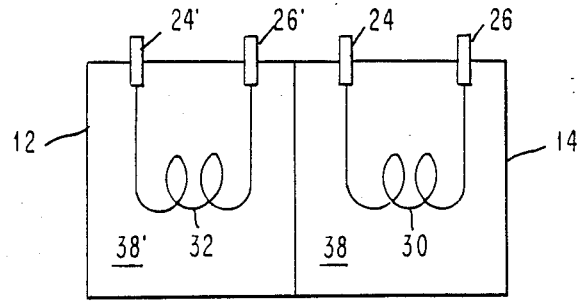

The overall GC system of FIG. 1, is operable in a plurality of different detector, injector, column configurations three of which are shown schematically in FIGS. 3-5. As shown in FIG. 3, a single injector 24 is operable in a split mode to simultaneously deliver the sample and carrier gas to columns 30 and 32 located in oven chambers 38 and 38' of ovens 14 and 14' respectively. The other end of column 30 is connected to detector 26 while the other end of column 32 is connected to detector 26'. Quite obviously, detectors 26 and 26' may be of different types, columns 30 and 32 may have different types of coatings to enable the separation of different constituents, and chambers 38 and 38' may be maintained at different temperatures or temperature programs. In FIG. 4, a single injector 24 on oven 12 is connected to one end of a capillary column which extends through both chambers 38' and 38 and is connected at its other end to detector 26. The column can be either a single column extending all the way through the walls between the two ovens or it may include separate columns 32 and 30 joined by a coupler 64. In FIG. 5, two completely independent detectors, injectors and columns are illustrated. This allows each of the ovens to be operated in a completely independent fashion either simultaneously or one at a time. The advantage is that the user in effect has the use of two separate GCs.

Figure 6:
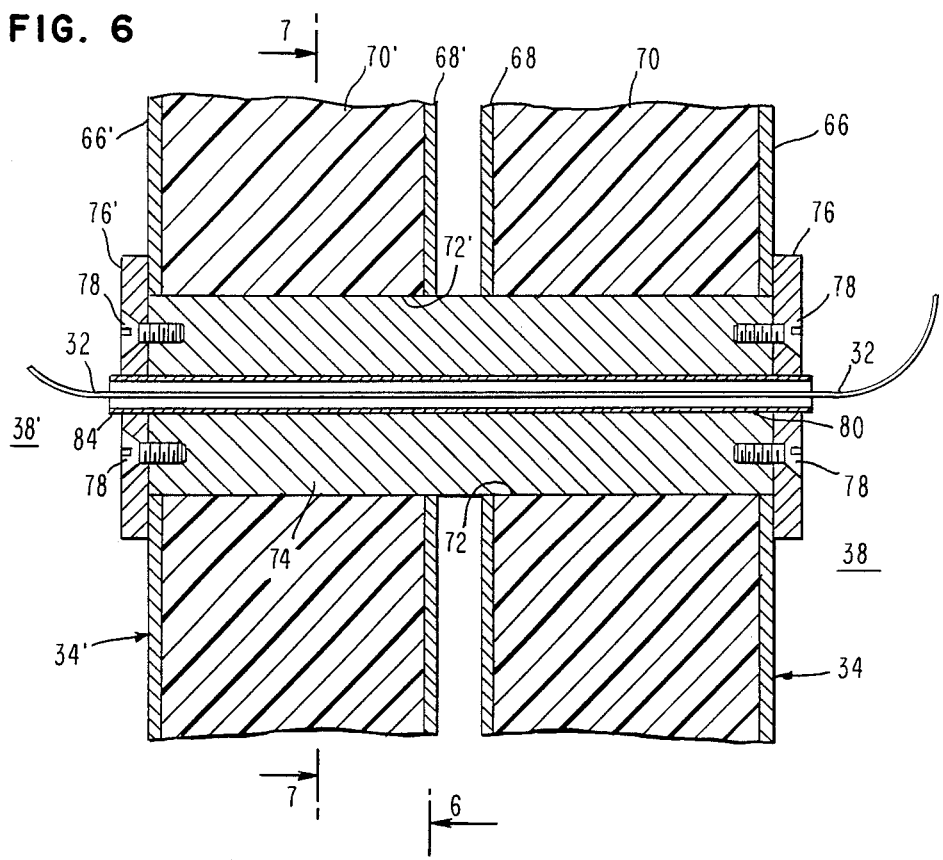
FIG. 6 is an enlarged cross-sectional view illustrating the connection between the two ovens.
Figure 7:
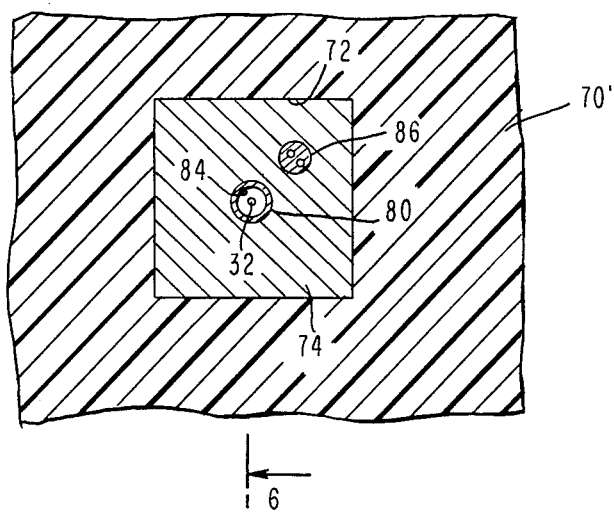
FIG. 7 is an enlarged sectional view looking along lines 7—7 of FIG. 6.

Referring to FIGS. 6 and 7, the walls of enclosure 34 are formed from an inner sheet metal layer 66 and outer sheet metal layer 68 on either side of insulation 70. An opening 72 is formed in the left side wall of enclosure 34 and an opening 72' is formed in the right side wall of enclosure 34'. An aluminum connector or block 74 of rectangular cross-section extends through the opening and is connected to circular plates 76 and 76' by screws 78 so as to physically connect enclosures 34 and 34', and hence ovens 14 and 14', together. A central opening 80 extends through block 74 and has a glass tube 84 extending therethrough, through which a portion of capillary column 32 extends. An electric cartridge heater 86 is embedded in block 74 and heats the block to a temperature preventing the condensation, within the portion of column 32 in block 74, of any gases flowing therethrough.

Figure 8:
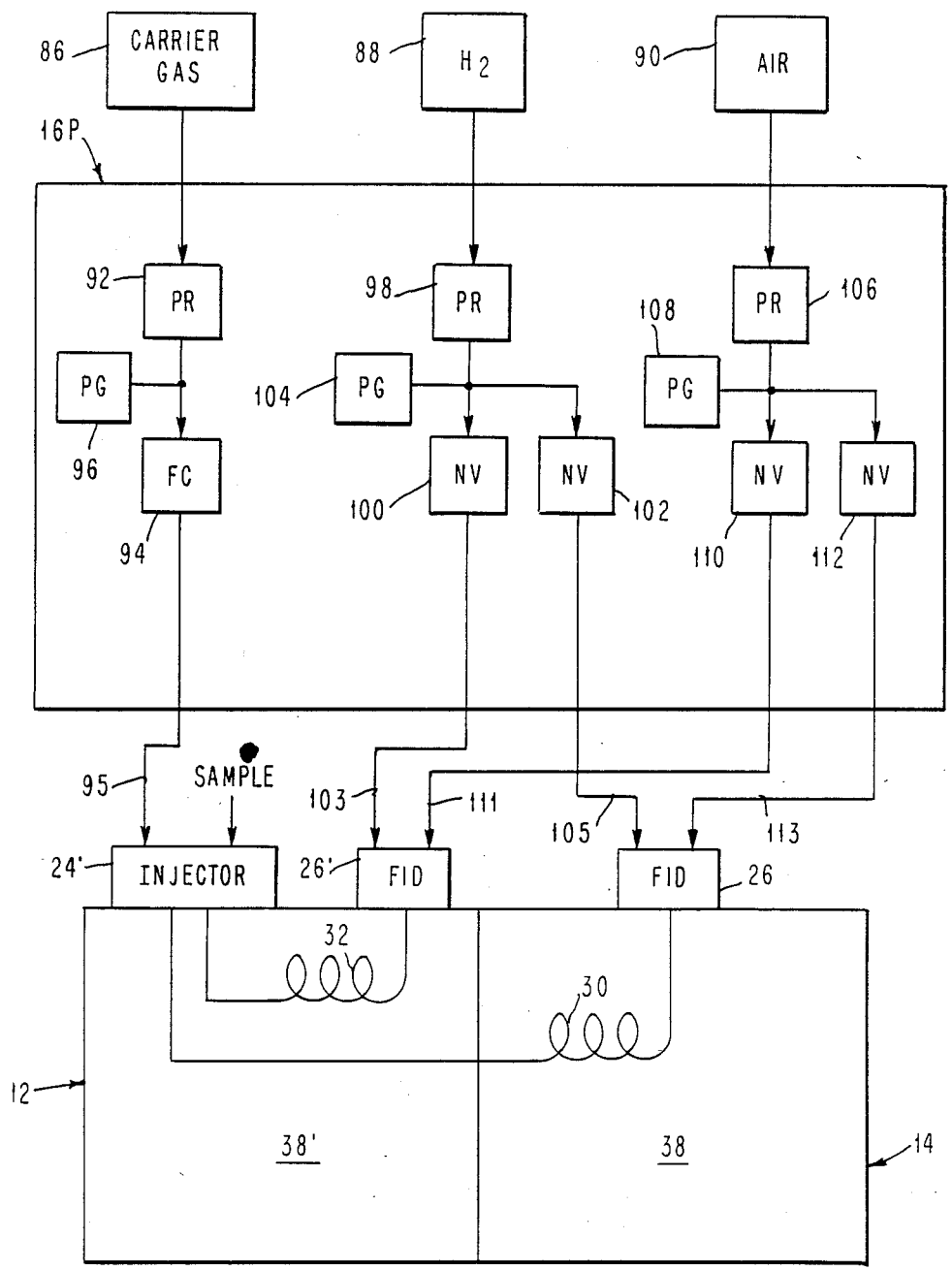
FIG. 8 is a schematic view of the gas control system of the GC system shown in FIG. 1.

As previously indicated, GC 10 includes a section 16 housing both electric and pneumatic controls. The pneumatic controls are designated as 16P in FIG. 8 and the electric controls as 16E in FIG. 9. The front panel of section 16 contains the various gauges, regulators, needle valves, etc., which are available to the user to adjust the flow rates of the gas or gases being used, as desired. It is to be understood that not all of these controls may be in use at any given time and that the ones used will depend upon the specific detector/injector column configuration. An example of one of configuration and mode of operation is illustrated in FIG. 8 wherein a injector 24' is mounted on oven 14' and provides a split flow of carrier gas, and a sample through columns 32 and 30. FIDs 26 and 26' are respectively mounted on ovens 14 and 14' and are connected to columns 30 and 32. A source 86 of carrier gas is located externally to GC 10. Carrier gas is fed through a line into an adjustable pressure regulator (PR) 92 of the pneumatic control section 16P. The output of carrier gas from PR 92 is fed through an adjustable flow controller (FC) 94 and through a connector line 95 to injector 24'. A pressure gauge (PG) 96 is connected to the flow line between PR 92 and FC 94 and is used in conjunction with PR 92 to allow the operator to adjust the pressure and the setting of FC 94 to achieve a desired flow rate. The carrier gas is preferably helium for use with capillary columns 30 and 32. Other carrier gases may also be used as appropriate.

The operation of a flame ionization detector requires that hydrogen ($H_2$) and air be supplied to the FID in conjunction with the sample and carrier gas flowing from the column. To accomplish this, a source 88 of hydrogen is connected through PR 98 to two needle valves (NV) 100, 102 which in turn respectively are connected to FID 26' and FID 26 to supply hydrogen thereto through connector lines 103, 105. A source 90 of air is connected to a PR 106 which in turn is connected to NVs 110 and 112 to supply air through connector lines 111, 113 respectively to FID 26' and 26. PGs 104 and 108 indicate the pressure within the hydrogen and air flow lines. For all of the gases, conventional filters (not shown) may be used to supply clean dry gas. It is important to note that the pneumatics control section 16P, which forms a part of GC10, is shared by both ovens 14' and 14. Section 16P is integrated with oven 14 and in the self-contained GC 10 can be used solely by oven 14. By the addition of oven 14', no additional pneumatic controls are required. This results in a cost reduction relative to that which would occur if the extra controls would have to be supplied. Connector lines 95, 103, 105, 111 and 113 are removable and relocatable to enable connections to be made for different injector-detector configurations.

Figure 9:
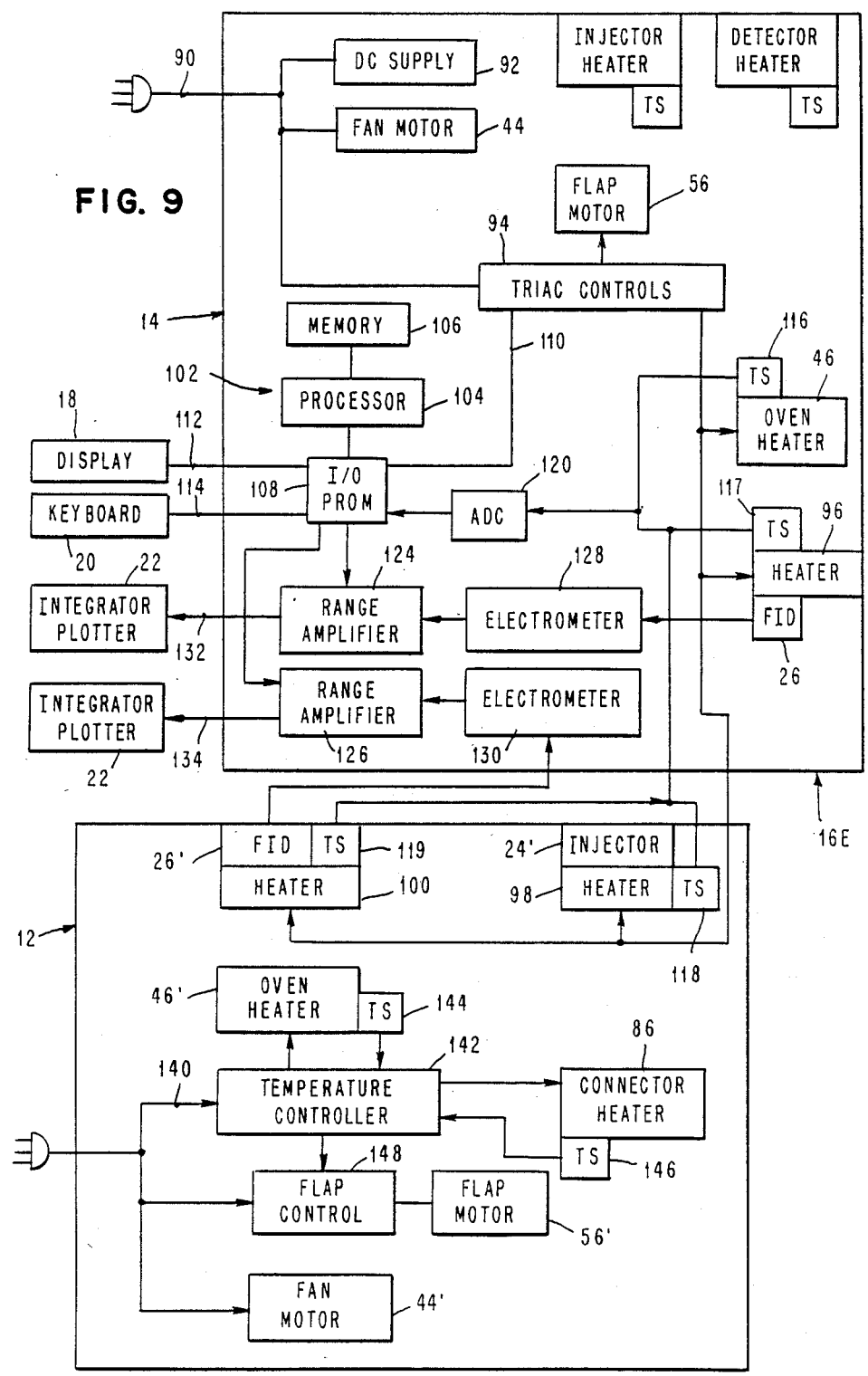
FIG. 9 is a schematic block diagram of the electrical control system of the GC system shown in FIG. 1.

Referring now to FIG. 9, the electrical section 16E of GC 10 is connectable by a power cord 90 to an external power line such as a 120 volt, 20 amp circuit. Cord 90 supplies power to a DC power supply 92 that converts the AC power into different levels of DC power for operating the various circuits. Cord 90 also supplies power directly to the fan motor 44 and to triac controls 94. The latter supply power to flap motor 56, oven heater 46, a heater 96 associated with the heater block for FID 26, a heater 98 associated with the heater block for injector 24' and a heater 100 associated with the heater block of FID 26'. The operation of triac controls 94 is under the control of a data processing system 102 which comprises a microprocessor or processor 104, a memory 106 and an I/O PROM 108 connected to various units being controlled by processor 104. A first connector 110 connects PROM 108 to triac controls 44 for supplying control signals thereto to operate motor 56 and the various heaters. PROM 108 is also connected by lines 112 and 114 to display 18 and keyboard 20 which act as interface between the user and GC 10. The user enters various commands, data and parameters, in conventional fashion, into such data systems to cause a desired procedure to be performed for analyzing a sample.

Associated with the various heaters are a plurality of temperature sensors (TS) 116-119 which provide analog signals indicative of the temperatures of the various ovens or zones being heated by the associated heaters. The various temperature sensors are each connected through an analog-to-digital converter (ADC) 120 to I/O PROM 108. Digital signals from ADC 120 are thereby fed into processor 104 and memory 106 to provide a feedback control via processor 104 and through controls 94, of the operation of the various heaters 46, 96, 98 and 100.

The user is able to enter via keyboard 20 the desired temperatures to be maintained or programmed.

PROM 108 is further connected to range amplifiers 124 and 126 to provide signals thereto adjusting the sensitivity or range of amplification of signals from the detectors. To accomplish this, FID 26 is connected to electrometer 128 which in turn is connected to amplifier 124. FID 26' is connected by electrometer 130 which is connected to amplifier 126. The outputs of amplifiers 124 and 126 are respectively fed by lines 132 and 134 to two integrator/plotters 22 which are operative to integrate and record the various signals from the detectors, in conventional fashion. It should be noted in the structure thus far described, that FID 26', heater 100 and heater 98, which are part of oven 14', share the electrical controls of section 16E and thus it is not necessary to have in GC 12 a separate data system or temperature controllers for the injector-detector ovens.

The remaining electrical portion of oven 14' is independent of the electrical portion 16E. It includes a power cord 140 connectable to an external source of power for supplying power via temperature controller 142 to oven heater 46' and connector heater 86. Temperature sensors 144 and 146 provide signals to controller 142 for controlling the temperature of the respective spaces being heated at the desired set points. Cord 140 also supplies power through flap control 148 to operate flap motor 56' in conjunction with a signal from temperature controller 142, to help regulate the interior temperature of oven 14'. Fan motor 44' is also connected to power cord 140. The advantage of providing the separate electrical controls particularly for oven heater 46', which is the element using the greatest amount of power, is that it allows cord 140 to be connected to a separate power line available to the user so that the user does not have to provide a higher capacity power line, which would otherwise be required if the electrical controls for both oven heaters 46 and 46' are all included in GC 10.

While the drawings illustrate only those elements or components used for exemplary detector injector-column configurations, it is to be understood that the systems 10 and 12 also include components that are unused for a given set-up. Preferably, each system includes two injector ovens and two detector ovens for supporting two injectors and two detectors. It should also be obvious to those skilled in the art that many changes can be made in the details and arrangement of parts without departing from the scope of the invention as defined in the appended claims.

Having thus described our invention, what we claim as new and desire to secure by Letters Patent is:

1. A double-oven gas chromatography (GC) system for separating samples into components by use of a plurality of GC columns connected to a plurality of injectors and detectors, comprising the combination of:
   a self-contained primary GC system operable in an independent manner and comprising
      a first oven comprising a first enclosure and a first door mounted on said first enclosure, said first door being movable between an open position and a closed position, said first oven having a first chamber therein defined by said first enclosure and said first door, said first door providing access to said first chamber when said first door is in said open position,
      first injector oven means mounted on said first oven and being adapted to support and independently heat a plurality of said injectors, first detector oven means mounted on said first oven and being adapted to support and independently heat a plurality of said detectors, an electrical system for controlling operation of said primary GC system and comprising a data system providing operator control over said primary GC system, said data system being connected to said detectors for analyzing output signals therefrom, and a pneumatic system for supplying and controlling the flow of any gas used to separate and analyze a sample, said pneumatic system being connected to said injectors;

and a secondary GC system added-on to said primary GC system and operable in only a dependent manner under the control of said primary GC system by sharing use of said electrical system and said pneumatic system, said secondary GC system comprising a second oven juxtaposed said first oven and comprising a second enclosure and a second door mounted on said second enclosure, said second door being movable between an open position and a closed position, said second oven having a second chamber therein defined by said second enclosure and said second door, said second door being movable independently of said first door and providing access to said second chamber independent of access to said first chamber, second injector oven means mounted on said second oven and being adapted to support and independently heat a plurality of said injectors, said second injector oven means comprising heater means and temperature sensing means connected to and operated by said electrical system of said primary GC system, and second detector oven means mounted on said second oven and being adapted to support and independently heat a plurality of said detectors, said second detector oven means comprising heater means and temperature sensing means connected to sand operated by said electrical system of said primary GC system;

said double-oven GC system being configurable in a plurality of injector-column-detector configurations in which at least one injector is mounted on said second injector oven means and at least one detector is mounted on said second detector oven means, said one injector being connected to said pneumatic system to receive gas therefrom, said one detector being connected to said electrical system and providing output signals thereto for analysis thereby.

2. The combinations of claim 1 wherein said first and second enclosures are box-shaped and each one includes a top wall, a bottom wall, an end wall and two side walls, one side wall of said first enclosure being adjacent to one side wall of said second enclosure;

said first and second doors being pivotally mounted on side walls of said enclosures opposite to said end walls to provide access to said first and second chambers from in front of said ovens;

said injector ovens and said detector ovens being mounted on said top walls of said enclosures.

3. The combustion of claim 2 wherein said second GC oven includes a heater and a temperature sensor, and said combination further includes a temperature controller connected to such heater and sensor for controlling the temperature in said second GC oven independently of the temperature in said first GC oven.

4. The combination of claim 3 wherein said temperature controller is connectable to a first power line and said electrical system is connectable to a different power line.

5. The combination of claim 2 further comprising:
connector means physically interconnecting said first and second ovens.

6. The combination of claim 5 wherein said first and second GC ovens are substantially identical.

7. The combination of claim 5 wherein said configurations comprise a first configuration in which a single column has end portions located within both of said chambers and a medial portion extending between said chambers, and said connector means has a passage extending through said adjacent side walls of said enclosures, said medial portion of said single column extending through said passage.

8. The combination of claim 7 further comprising:
a heater for beating said connector means and said medial portion to prevent condensation of any sample constituent therein.

* * * * *